(12) United States Patent
Ambwani et al.

(10) Patent No.: US 9,996,921 B2
(45) Date of Patent: Jun. 12, 2018

(54) DETECTION OF METAL STENT STRUTS

(71) Applicant: LightLab Imaging, Inc., Westford, MA (US)

(72) Inventors: Sonal Ambwani, Westborough, MA (US); Christopher E. Griffin, Wilton, NH (US)

(73) Assignee: LIGHTLAB IMAGING, INC., Westford, MA (US)

( * ) Notice: Subject to any disclaimer, the term of this patent is extended or adjusted under 35 U.S.C. 154(b) by 0 days. days.

(21) Appl. No.: 14/975,516

(22) Filed: Dec. 18, 2015

(65) Prior Publication Data

US 2016/0335763 A1    Nov. 17, 2016

Related U.S. Application Data

(60) Provisional application No. 62/162,795, filed on May 17, 2015, provisional application No. 62/196,997, filed on Jul. 25, 2015.

(51) Int. Cl.
| | |
|---|---|
| *G06T 7/00* | (2017.01) |
| *A61B 5/00* | (2006.01) |
| *A61B 5/06* | (2006.01) |
| *G06T 7/70* | (2017.01) |
| *G06K 9/46* | (2006.01) |

(52) U.S. Cl.
CPC .......... *G06T 7/0012* (2013.01); *A61B 5/0066* (2013.01); *A61B 5/0084* (2013.01); *A61B 5/06* (2013.01); *A61B 5/6852* (2013.01); *G06K 9/4647* (2013.01); *G06T 7/70* (2017.01); *G06K 2209/05* (2013.01); *G06T 2207/10068* (2013.01); *G06T 2207/10101* (2013.01); *G06T 2207/30021* (2013.01); *G06T 2207/30052* (2013.01); *G06T 2207/30101* (2013.01)

(58) Field of Classification Search
CPC ................. G06T 7/0012; G06T 7/0042; G06T 2207/10101; G06T 2207/30101
USPC ......................................................... 382/182
See application file for complete search history.

(56) References Cited

U.S. PATENT DOCUMENTS

| | | |
|---|---|---|
| 4,548,473 A | 10/1985 | Lo et al. |
| 5,054,492 A | 10/1991 | Scribner et al. |
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |

(Continued)

FOREIGN PATENT DOCUMENTS

| | | |
|---|---|---|
| EP | 2062526 | 5/2009 |
| JP | 63-127201 | 5/1988 |

(Continued)

OTHER PUBLICATIONS

Wang et al: "Automatic stent strut detection in intravascular optical coherence tomographic pullback runs", Int. J. Cardiovasc Imaging, 2013.*

(Continued)

*Primary Examiner* — Ruiping Li
(74) *Attorney, Agent, or Firm* — K&L Gates LLP

(57) ABSTRACT

The disclosure relates to stent detection and shadow detection in the context of intravascular data sets obtained using a probe such as, for example, and optical coherence tomography probe or an intravascular ultrasound probe.

20 Claims, 5 Drawing Sheets

(56) References Cited

U.S. PATENT DOCUMENTS

| | | |
|---|---|---|
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,670,603 B2 | 3/2014 | Tolkowsky et al. |
| 8,687,201 B2 | 4/2014 | Adler |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,786,336 B1 | 7/2014 | Schmitt |
| 8,831,321 B1 | 9/2014 | Elbasiony |
| 8,855,744 B2 | 10/2014 | Tolkowsky et al. |
| 8,909,323 B2 | 12/2014 | Baumgart |
| 8,913,084 B2 | 12/2014 | Chen et al. |

(56) References Cited

U.S. PATENT DOCUMENTS

| | | |
|---|---|---|
| 8,948,228 B2 | 2/2015 | Adler |
| 8,953,911 B1 | 2/2015 | Xu et al. |
| 8,983,580 B2 | 3/2015 | Boppart et al. |
| 9,069,396 B2 | 6/2015 | Adler et al. |
| 9,173,591 B2 | 11/2015 | Elbasiony |
| 9,308,052 B2 | 4/2016 | Tolkowsky et al. |
| 9,351,698 B2 | 5/2016 | Dascal et al. |
| 9,404,731 B2 | 8/2016 | Adler et al. |
| 9,435,956 B1 | 9/2016 | Xu et al. |
| 9,488,464 B1 | 11/2016 | Schmitt |
| 9,629,571 B2 | 4/2017 | Tolkowsky et al. |
| 2002/0115931 A1 | 8/2002 | Strauss et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2005/0238067 A1 | 10/2005 | Choi |
| 2005/0249391 A1 | 11/2005 | Kimmel et al. |
| 2006/0095065 A1 | 5/2006 | Tanimura et al. |
| 2006/0135870 A1 | 6/2006 | Webler |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0024617 A1 | 2/2007 | Poole |
| 2007/0060822 A1 | 3/2007 | Alpert et al. |
| 2007/0066890 A1 | 3/2007 | Maschke |
| 2007/0115481 A1 | 5/2007 | Toth et al. |
| 2007/0123771 A1 | 5/2007 | Redel et al. |
| 2007/0135803 A1 | 6/2007 | Belson |
| 2007/0165916 A1 | 7/2007 | Cloutier et al. |
| 2007/0167710 A1 | 7/2007 | Unal et al. |
| 2007/0232933 A1 | 10/2007 | Gille et al. |
| 2007/0260198 A1 | 11/2007 | Atlas |
| 2007/0293932 A1 | 12/2007 | Zilla et al. |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0228086 A1 | 9/2008 | Ilegbusi et al. |
| 2008/0281205 A1 | 11/2008 | Naghavi et al. |
| 2009/0027051 A1 | 1/2009 | Stuber et al. |
| 2009/0174931 A1 | 7/2009 | Huber et al. |
| 2009/0204134 A1 | 8/2009 | Kassab |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank et al. |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1 | 9/2011 | Eichler |
| 2011/0257545 A1 | 10/2011 | Suri |
| 2011/0319752 A1 | 12/2011 | Steinberg et al. |
| 2012/0004529 A1 | 1/2012 | Tolkowsky et al. |
| 2012/0029339 A1 | 2/2012 | Cohen et al. |
| 2012/0057157 A1 | 3/2012 | Petersen et al. |
| 2012/0075638 A1* | 3/2012 | Rollins ............ A61B 1/00009 356/479 |
| 2012/0162660 A1 | 6/2012 | Kemp |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2012/0310081 A1 | 12/2012 | Adler et al. |
| 2013/0006105 A1 | 1/2013 | Furuichi |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |
| 2013/0303910 A1 | 11/2013 | Hubbard et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0094697 A1 | 4/2014 | Petroff et al. |
| 2014/0114182 A1 | 4/2014 | Petersen et al. |
| 2014/0114184 A1 | 4/2014 | Klaiman et al. |
| 2014/0114185 A1 | 4/2014 | Tolkowsky et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0257087 A1* | 9/2014 | Elbasiony ............ A61B 5/061 600/424 |
| 2014/0268167 A1 | 9/2014 | Friedman et al. |
| 2014/0270445 A1 | 9/2014 | Kemp |
| 2014/0276011 A1 | 9/2014 | Schmitt et al. |
| 2014/0276020 A1 | 9/2014 | Hutchins et al. |
| 2014/0309536 A1 | 10/2014 | Douk et al. |
| 2014/0379269 A1 | 12/2014 | Schmitt |
| 2015/0153157 A1 | 6/2015 | Schmitt et al. |
| 2015/0119707 A1 | 7/2015 | Schmitt |
| 2015/0192405 A1 | 7/2015 | Schmitt |
| 2015/0297373 A1 | 10/2015 | Schmitt et al. |
| 2015/0370229 A1 | 12/2015 | Adler et al. |
| 2016/0000406 A1 | 1/2016 | Petroff |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2016/0073885 A1 | 3/2016 | Adler |
| 2016/0174925 A1 | 6/2016 | Dascal et al. |
| 2016/0313507 A1 | 10/2016 | Adler et al. |
| 2016/0335763 A1 | 11/2016 | Ambwani et al. |
| 2016/0335766 A1 | 11/2016 | Ambwani et al. |

FOREIGN PATENT DOCUMENTS

| | | |
|---|---|---|
| WO | 2006076409 | 7/2006 |
| WO | 2007002685 | 1/2007 |
| WO | 2011038044 | 3/2011 |
| WO | 2012126070 | 9/2012 |
| WO | 2012176191 | 12/2012 |
| WO | 2013175472 | 11/2013 |
| WO | 2014002095 | 3/2014 |
| WO | 2014137353 | 9/2014 |

OTHER PUBLICATIONS

Briguori et al., "Intravascular ultrasound criteria for the assessment of the functional significance of intermediate coronary artery stenoses and comparison with fractional flow reserve," Am J. Cardiol 87:136-141, 2001.

(56) References Cited

OTHER PUBLICATIONS

Kassab et al., "The pattern of coronary arteriolar bifurcations and the uniform shear hypothesis," Annals of Biomedical Engineering 23 (1): 13-20, 1995.
Hariri et al., "An automatic image processing algorithm for initiating and terminating intracoronary OFDI pullback" Biomedical Optics Express 1:2 566-573 (Sep. 1, 2010).
Harrison et al., "The value of lesion cross-sectional area determined by quantitative coronary angiography in assessing be physiologic significance of proximal left anterior descending coronary arterial stenoses," Circulation 69:6 1111-1119, 1984.
Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.
Kolyva et al., "Increased diastolic time fraction as beneficial adjunct of α1-adrenergic receptor blockade after percutaneous coronary intervention," Am J Physiol Heart Circ Physiol 295: H2054-H2060, 2008.
Kolyva et al., "'Windkesselness' of coronary arteries hampers assessment of human coronary wave speed by single-point technique," Am J Physiol Heart Circ Physiol, 295: H482-H490, 2008.
Laslett, "Normal left main coronary artery diameter can be predicted from diameters of its branch vessels," Clinical Cardiology 18 (10): 580-582, 1995.
Ofili et al., "Differential characterization of blood flow, velocity, and vascular resistance between proximal and distal formal epicardial human coronary arteries: analysis by intracoronary Doppler spectral flow velocity," Am Heart J. 130:1 37-46, 1995.
Ohta et al., "Rheological Changes After Stenting of a Cerebral Aneurysm: A Finite Element Modeling Approach," Cardiovascular and Interventional Radiology (2005) 28:768-772.
Pijls et al., "Fractional Flow Reserve (FFR) Post-Stent Registry Investigators Coronary pressure measurement after stenting predicts adverse events at follow-up: a multicenter registry", Circulation 2002; 105:2950-2954.
Seiler et al., "Basic structure-function relations of the epicardial coronary vascular tree, Basis of quantitative coronary arteriography for diffuse coronary artery disease," Circulation 85 (6): 1987-2003, 1992.
Siebes et al., "Single-wire pressure and flow velocity measurement to quantify coronary stenosis hemodynamics and affects of percutaneous interventions," Circulation 109:756-762, 2004.
Sihan et al., "A Novel Approach to Quantitative Analysis of Intravascular Optical Coherence Tomography Imaging," Computers in Cardiology 2008; 35:1089-1092.
Sihan et al., "Fully Automatic Three-Dimensional Quantitative Analysis of Intracoronary Optical Coherence Tomography: Method and Validation," Catheterization and Cardiovascular Interventions 74:1058-1065 (2009).
Spaan, "Coronary Blood Flow," Ch 12. Dordrecht, The Netherlands: Kluwer Acedemic Publishers, Boston; 1991: pp. 333-361.
Takagi et al., "Clinical potential of intravascular ultrasound for physiological assessment of coronary stenosis," Circulation 100: 250-255, 1999.
Verhoeff et al., "Influence of percutaneous coronary intervention on coronary microvascular resistance index," Circulation 111:76-82, 2005.
White et al., "Does visual interpretation of the coronary angiogram predict the physiologic importance of coronary stenoses?," N. Engl J Med 310:13 819-824, 1984.
Wilson et al., "Prediction of the physiologic significance of coronary arterial lesions by quantitative lesion geometry in patients with limited coronary artery disease," Circulation 75: 723-732, 1987.
Perez-Rovira et al., "Deformable Registration of Retinal Fluorescein Angiogram Sequences Using Vasculature Structures", 32nd Annual Conf. of IEEE EMBS, 2010, pp. 4383-4386.
Herrington et al., "Semi-automated boundary detection for intravascular ultrasound," Computers in Cardiology 1992 Proceedings., pp. 103-106, Oct. 1992.
Sonka et al., "Segmentation of intravascular ultrasound images: a knowledge-based approach," IEEE Transactions on Medical Imaging, 14(4):719-732, Dec. 1995.
Mojsilovic et al., "Automatic segmentation of intravascular ultrasound images: A texture-based approach," Annals of Biomedical Engineering, 25:1059-1071, Nov. 1997.
Gil et al., "Automatic segmentation of artery wall in coronary IVUS images: a probabilistic approach," Computers in Cardiology 2000; 27:687-690.
Haas et al., "Segmentation of 3D intravascular ultrasonic images based on a random field model," Ultrasound in Medicine & Biology, 26:2, 297-306, 2000.
Kovalski et al., "Three-dimensional automatic quantitative analysis of intravascular ultrasound images," Ultrasound in Medicine & Biology, 26(4):527-537, 2000.
Pujol et al., "Intravascular Ultrasound Images Vessel Characterization using AdaBoost," Functional Imaging and Modeling of the Heart: Lecture Notes in Computer Science, pp. 242-251, 2003.
Taki et al., "Automatic segmentation of calcified plaques and vessel borders in IVUS images," International Journal of Computer Assisted Radiology and Surgery, 3(3-4):347-354, Sep. 2008.
van den Berg et al., "Using three-dimensional rotational angiography for sizing of covered stents," Am. J. Roentgenology, 178:149-152 (2002).
Wong et al., "A novel method of coronary stent sizing using intravascular ultrasound: safety and clinical outcomes," Int. J. Angiol. , 18(1): 22-24 2009.
Bonnema et al., "An automatic algorithm for detecting stent endothelialization from volumetric optical coherence tomography datasets", Physics in Medicine and Biology, 53 :12, Jun. 21, 2008, pp. 3083-3098.
Unal et al., "Stent implant follow-up in intravascular optical coherence tomography images," Int J Cardiovasc Imaging, DOI 10.1007/s10554-009-9508-4, published online Sep. 24, 2009, 8 pgs.
Xu et al., "Characterization of atherosclerosis plaques by measuring both backscattering and attenuation coefficients in optical coherence tomography," Journal of Biomedical Optics, 13:3, May/Jun. 2008, 8 pgs.
Takano et al.. "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.
Tung et al., "Automatic Detection of Coronary Stent Struts in Intravascular OCT Imaging," Proceedings of SPIE, vol. 8315, Feb. 22, 2012 (8 pgs.).
Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.
Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.
Dave Fornell, "The Advantages and Disadvantages of OCT vs. IVUS", Diagnostic and Interventional Cardiology, May 18, 2011, pp. 1-4.
International Search Report and Written Opinion of the International Searching Authority for International application No. PCT/US2016/032908, dated Sep. 23, 2016 (13 pages).

* cited by examiner

DETECTION OF METAL STENT STRUTS

CROSS-REFERENCE TO RELATED APPLICATIONS

This application claims priority to and the benefit of U.S. Provisional Patent Application No. 62/162,795 filed on May 17, 2015 and U.S. Provisional Patent Application No. 62/196,997 filed on Jul. 25, 2015, the disclosures of which are herein incorporated by reference in their entirety.

FIELD

The disclosure relates to systems and methods for shadow analysis and stent detection.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs, as well as implanted medical devices such as stents.

Stents are a common intervention for treating vascular stenoses. It is critical for a clinician to develop a personalized stent plan that is customized to the patient's vascular anatomy to ensure optimal outcomes in intravascular procedures. Stent planning encompasses selecting the length, diameter, and landing zone for the stent with an intention to restore normal blood flow to the downstream tissues. Clinicians often reimage a stented vessel immediately after stent implantation to confirm that stent placement is correct. Clinicians also reimage stented vessels as routine follow up for stent interventions.

Stent detection methods typically detect individual metal stent struts by first detecting shadows cast by the struts onto the blood vessel wall to localize the region of search and then detect the location of the strut within the detected shadows. However, existing methods are inadequate and often result in missed struts or in the detection of false positive struts.

The present disclosure addresses the need for enhanced detection of metal stent struts.

SUMMARY

Disclosed herein are systems and methods for precise identification of metal stent strut offsets, or locations, within shadows cast in OCT image data. Methods of stent strut detection can include accessing a plurality of frames of intravascular imaging data, the plurality of frames comprising optical coherency tomography (OCT) scan lines, identifying a shadow region corresponding to a candidate stent strut, identifying scan lines that correspond to a candidate stent strut shadow region to generate candidate strut shadow scan lines, and analyzing the candidate strut shadow scan lines to identify the location of a stent strut.

Methods of stent strut detection also can include storing a plurality of frames of intravascular imaging data, detecting stent struts in a first group of frames of the plurality of frames, detecting one or more shadow regions in the first group of frames, wherein one or more of the shadow regions is adjacent to a detected stent strut, determining on a per shadow region basis if a given shadow region is a guidewire induced region or a side branch induced region to generate a set of candidate stent strut shadow regions, wherein each candidate stent strut shadow region comprises a shadow boundary, and identifying scan lines of a candidate stent strut shadow region within the shadow boundary.

Methods of the invention can include additional steps or features. For example, the methods can include identifying a shadow region corresponding to a candidate stent strut by eliminating shadow regions corresponding to non-stent features. The non-stent features can be selected, for example, from the group consisting of: a guidewire, a side branch, and combinations thereof.

The methods can include eliminating candidate strut shadow scan lines that contain spillage from lumen pixels.

The methods can include determining a projection across each of the candidate strut shadow scan lines by summing a signal response across the candidate strut shadow scan lines, or a portion or sample of the scan lines.

The methods can include identifying up to three local maxima in the projection.

The methods can include ranking local maxima based on peak signal intensity to generate a peak score. The ranking can be an ordinal ranking, with local maxima having higher peak signal intensity receiving a higher peak score.

The methods can include ranking the local maxima based on proximity to the blood vessel wall to generate a proximity score. The ranking can be an ordinal ranking, with local maxima closer to the blood vessel wall receiving a higher proximity score.

The methods can include assigning a malapposition score to each local maxima.

The malapposition score can be binary, with malapposed local maxima receiving a score of zero.

The methods can include summing the peak score, the proximity score, and the malappostion score, wherein the local maximum with the highest total score is designated as the location of the stent strut.

The methods can include identifying a plurality shadow region corresponding to a candidate stent strut, identifying scan lines that correspond to each candidate stent strut shadow region, and identifying, within each candidate stent strut shadow region, the location of a stent strut.

The methods can include performing a cross-frame analysis to validate designated stent struts across multiple optical coherence tomography (OCT) imaging frames.

The methods can include displaying on a graphical user interface the validated stent struts.

The invention also includes a computer readable medium comprising non-transitory instructions that when executed cause a processor to perform any of the foregoing steps.

BRIEF DESCRIPTION OF DRAWINGS

The figures are not necessarily to scale, emphasis instead generally being placed upon illustrative principles. The FIG. 1A is an exemplary intravascular data collection system and an associated intravascular data collection probe and related image processing, detection, and other software components according to an illustrative embodiment of the disclosure.

DETAILED DESCRIPTION

The disclosure provides, in part, methods and systems for identifying within a detected stent shadow the precise offset, or location, of the strut resulting in the detected shadow. Sometimes, within a shadow there is a single possible strut location corresponding to a bright strut bloom, or peak, against a dark shadow background in the scan line. However, multiple strut peaks often are detected inside a strut shadow, making it difficult to identify the exact location of a stent strut. Spurious peaks can be caused by, for example, blood pooling, poor blood clearing in the pullback zone, or ringing artifacts due to the imaging optics interacting with the metal strut. The present disclosure provides methods and systems for identifying the best candidate for a true stent within a stent shadow.

Figure 1A:
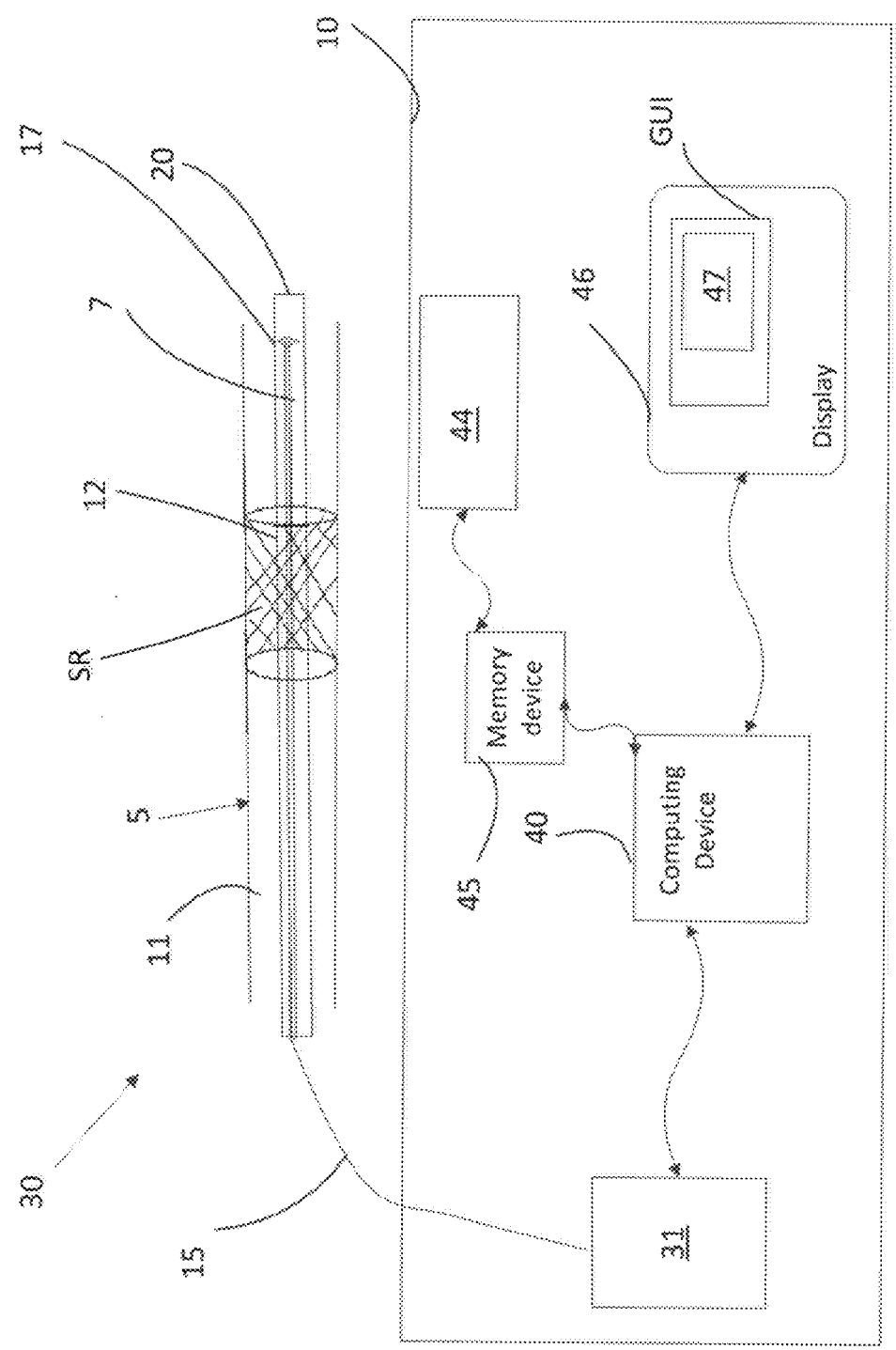
FIG. 1B is a cross-sectional OCT image of a stented blood vessel in accordance with an illustrative embodiment of the disclosure.

FIG. 1A is a high level schematic diagram depicting a blood vessel 5, such as an artery, a data collection probe 7 and an intravascular data collection and processing system 10. The system 10 can include for example, an OCT, intravascular ultrasound (IVUS), or other intravascular imaging system. A stent 12 is shown in the blood vessel 5. The stent includes a plurality of struts. Some of the struts can generate shadows or shadow regions SR as part of the process of imaging the vessel with an intravascular probe. The system 10 can include various software modules suitable for performing side branch detection, peak detection, shadow region detection and processing, error correction, model comparisons, lumen detection, and various other processes as described herein. The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls of the blood vessel 5. The walls of the blood vessel 5 define a lumen boundary. This lumen boundary can be detected using the distance measurements obtained from the optical signals collected at the probe tip 17 using lumen detection software component. Side branches and stent struts and shadow regions and other features can be identified in the scan lines generated during a pullback through the artery by the probe. The probe 7 can include other imaging modalities in addition to OCT such as ultrasound in one embodiment. In one embodiment, the lumen/lumen boundary refers to a portion of the vessel that is first impinged upon when light or ultrasound exists an intravascular imaging probe that generates a signal of interest for imaging the vessel. This excludes any blood flowing in the vessel which is typically removed using image processing in the form of masking. In one embodiment, the lumen or lumen boundary refers to a region of tissue that is disposed in front of the vessel wall and facing the blood containing region of the vessel.

Figure 1B:
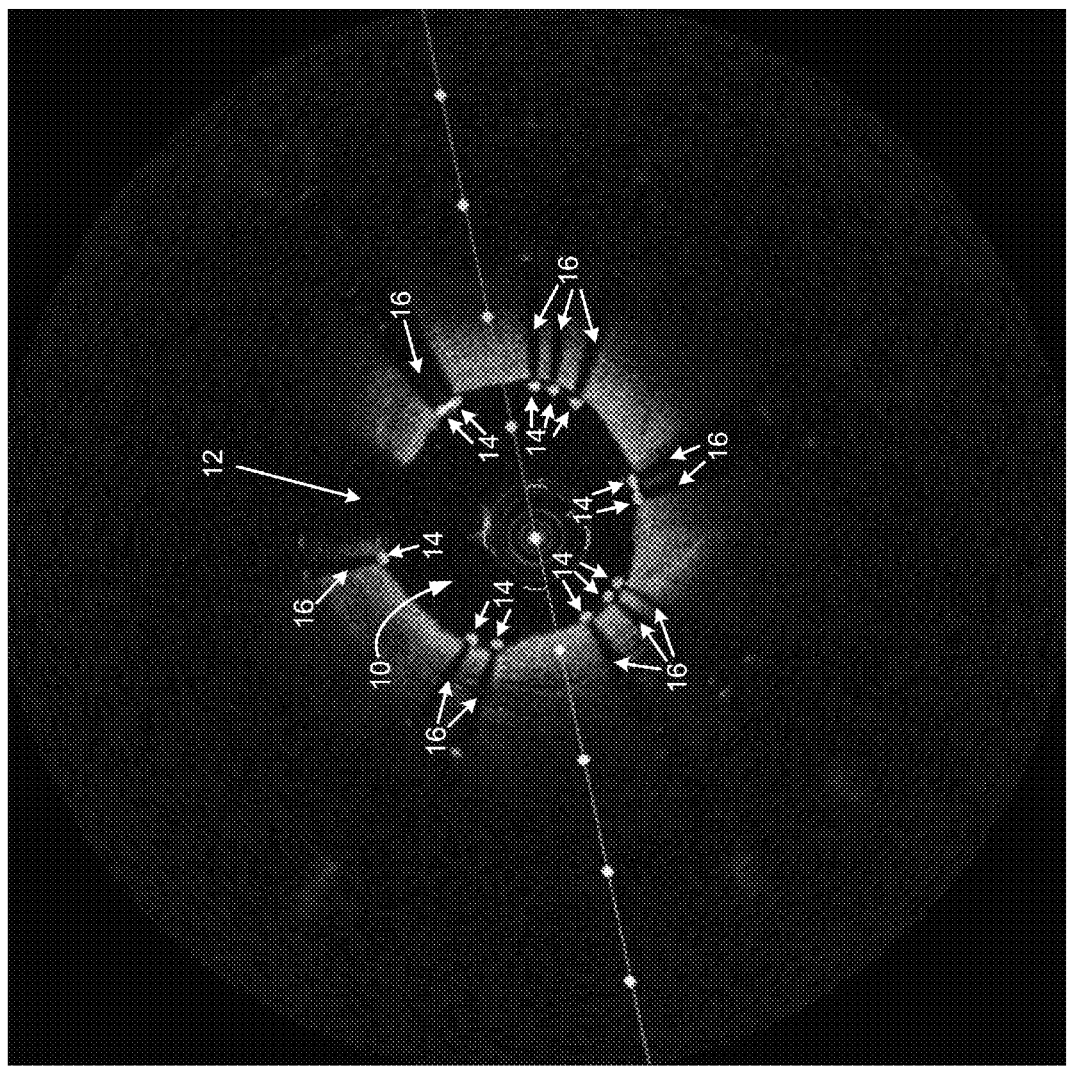

As shown in FIG. 1A, the probe tip 17 is positioned in the lumen 14 such that it is distal to a stented region of the blood vessel 5. The probe tip 17 is configured to transmit light and receive backscattered light from objects, such as for example stent 12, and the wall of the blood vessel 5. The probe tip 17 and the rest of the data collection probe 7 are pulled through the lumen 14. As shown in FIG. 1B, a probe 17 is shown prior to or after insertion in a blood vessel. The probe 7 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for side branch detection, stent strut candidate selection or identification, candidate stent strut shadow region detection, correlations and comparisons of stent image data stent visualization, and pullback data collection as discussed below.

In one embodiment, the computing device 40 includes or accesses software modules or programs 44, such as a side branch detection module, a lumen detection module, a stent detection module, a stent strut validation module, a candidate stent strut identification module and other software modules. The software modules or programs 44 can include an image data processing pipeline or component modules thereof and one or more graphical user interfaces (GUI). The modules can be subsets of each other and arranged and connected through various inputs, outputs, and data classes.

An exemplary image processing pipeline and components thereof can constitute one or more software programs or modules 44. The software modules 44 may comprise several image processing algorithms tailored to detect the vessel lumen, side-branches, guide-wires, guide-catheters, stent struts and stent regions. This disclosure relates to image processing to determine the location of a metal strut within its shadow. The image data processing pipeline, its components software modules and related methods and any of the methods described herein are stored in memory and executed using one or more computing devices such as a processor, device, or other integrated circuit.

As shown, in FIG. 1A, a display 46 can also be part of the system 10 for showing information 47 such as cross-sectional and longitudinal views of a blood vessel generated from OCT or IVUS imaging data. The image processing software algorithms 44 provide data corresponding to detected image features such as stents, side-branches, guide-wire etc. and this data is input to the GUI where these features are displayed in a desired format on cross-sectional, longitudinal, and/or 3D display sections of the GUI. The image of FIG. 1B is an example of display information 47 that can be displayed and interacted with using a GUI and various input devices. Specifically, it shows a 2D cross-sectional view of a coronary artery containing a metal stent.

In addition, display information 47 can include, without limitation, cross-sectional scan data, longitudinal scans, diameter graphs, image masks, stents, areas of malapposition, lumen border, and other images or representations of a blood vessel or the underlying distance measurements obtained using an OCT system and data collection probe. The computing device 40 can also include software or programs 44, which can be stored in one or more memory devices 45, configured to identify stent struts and malapposition levels (such as based on a threshold and measured distance comparison), shadow regions, and struts within shadow regions and other blood vessel features such as with text, arrows, color coding, highlighting, contour lines, or other suitable human or machine readable indicia.

FIG. 1B is a cross-sectional OCT image of a stented blood vessel, in accordance with the present disclosure. The lumen/lumen boundary of the blood vessel 10 is in the center of the image. The guide wire shadow 12 is visible at the top of the image, from 12 to 1 o'clock. Also visible in FIG. 1B are multiple metal stent struts 14, which cast shadows 16 in the OCT image. Metal stent struts cast shadows against the blood vessel wall because the coherent light typically used for OCT imaging cannot penetrate stent struts but is reflected. The present disclosure provides enhanced methods for detecting the precise offset of struts within strut shadows.

Figure 2:
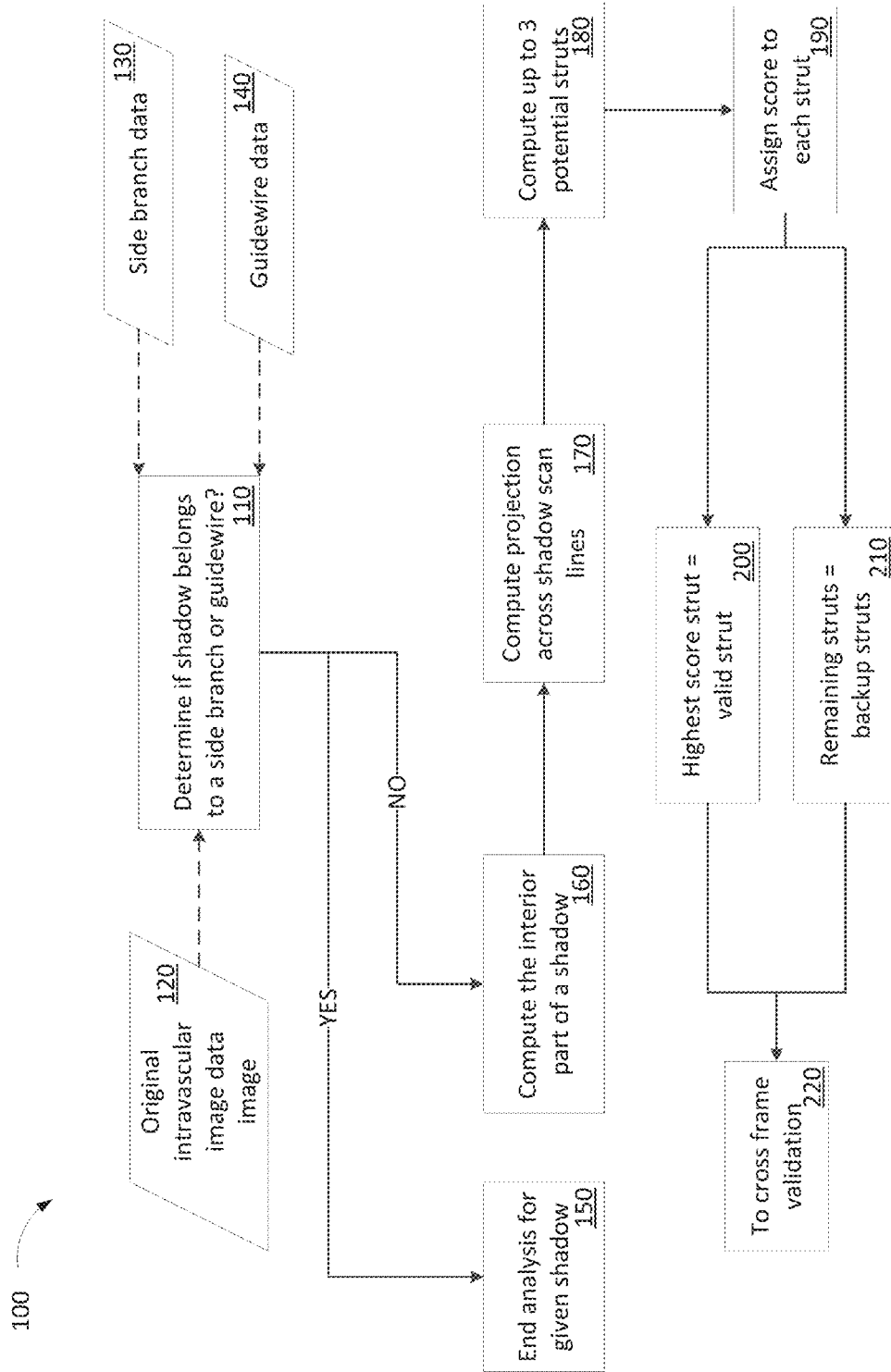
FIG. 2 is a process flow chart for detecting struts in OCT image data in accordance with an illustrative embodiment of the disclosure.

FIG. 2 is a process flow chart for detecting struts in OCT image data. The method 100 analyzes shadows corresponding to stent struts in a plurality of OCT pullback frames. The method 100 can include one or more of the steps described herein. Unless otherwise required, the steps can be performed in any order. The metal strut detection method operates upon various inputs from other image/intravascular data processing modules such as information about guide-wire (140), side-branch (130) and strut shadow locations (110). The process flow and associated method steps and stage can operate upon original intravascular data or raw data 120 obtained using a OCT, IVUS, or other intravascular data collection system. In one embodiment, data 120 has been processed by one or more image processing modules in a pipeline configuration.

In Step 110, each shadow in the OCT image data is cross-examined with data inputs from a side branch detection module 130 and a guide-wire detection module 140 to determine if the shadow is attributable to a side branch vessel or guidewire. Methods, systems, and devices for detecting strut shadows, side branches, and guidewire shadows are known. See, e.g., U.S. Pat. Nos. 8,412,312; 8,478,387; 8,831,321; 9,138,147 and 9,173,591.

At Step 150, if a given shadow is determined to be attributable to the guidewire or a side branch, the shadow is discarded and the analysis ends with respect to that shadow. At Step 160, if a given shadow is determined to be attributable to a stent strut, either by direct detection or by process of elimination, the shadow is analyzed to compute, or isolate, the interior part of the shadow. The shadow boundaries are trimmed away such that only the scan lines, or A-Lines, corresponding to the interior (and hence the "darkest") portion of the shadow are retained. The reason for this is that the shadow region, specifically the start and stop scan lines of the shadow, can sometimes contain spillage from the neighboring lumen pixels. Isolating the interior of the shadow and ignoring transitionary scan lines at the shadow margins improves assessment of strut offsets.

At step 170, the shadow interior is analyzed to compute the projection (or sum) of each sample across scan lines corresponding to the interior part of the shadow. Each scan-line is sampled into discrete pixels or "samples". In the input OCT image data, each scan line refers to data acquired along a particular angular direction with the imaging catheter at the center. Each scan line is in turn radially sampled into a discrete set of pixels or "samples". Each sample in the OCT data is typically a few microns wide and is typically uniform in size. A "projection" refers to the process of adding across each scan line. In other words, the 2-dimensional shadow in the {scan-line, sample} space is collapsed into a 1-dimensional signal where the i-th index corresponds to the sum of the i-th sample of each scan-line involved in the process. The projection contains samples, at radius R, which are the average of samples from the constituent scanlines at that same radius R.

At step 180, the projection is searched for up to three (e.g., 1, 2, or 3) of the largest local maxima. The location, or offset, of each selected maximum may be noted as potential strut locations, and certain features of the selected maxima are then analyzed to determine which one is the best candidate for being a true strut. In various embodiments, only the largest maximum is selected. In other embodiments, two or three of the largest maxima are selected. The initial selection of multiple local maxima increases sensitivity. Although more than three local maxima can be selected, this typically is unnecessary because one of the three highest maxima usually indicates the true strut location. The maxima selection process is illustrated by FIGS. 3A and 3B.

Figure 3A:
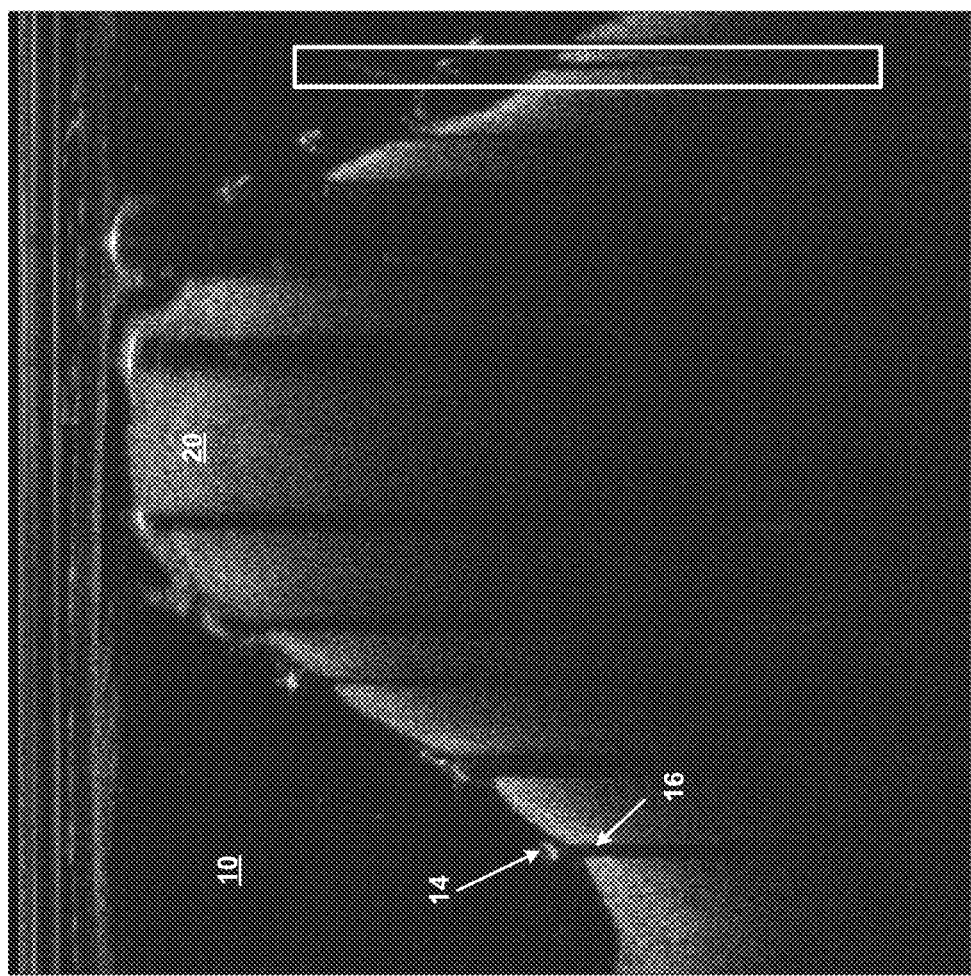
FIG. 3A is a scan line OCT image in polar co-ordinates, in log scale, of a stented vessel in accordance with an illustrative embodiment of the disclosure.

FIG. 3A is an A-Line OCT image, in log scale, of a stented vessel. The box on the right of the image indicates a shadow under analysis, and FIG. 3B shows a projection graph for this shadow. The blood vessel lumen 10 is the dark region at the top of the image, and the blood vessel wall 18 is the bright region at the bottom of the image. Multiple stents 14 and stent shadows 16 are visible in the image. In one embodiment, the lumen is the boundary between the tissue and the cleared interior of the vessel.

Figure 3B:
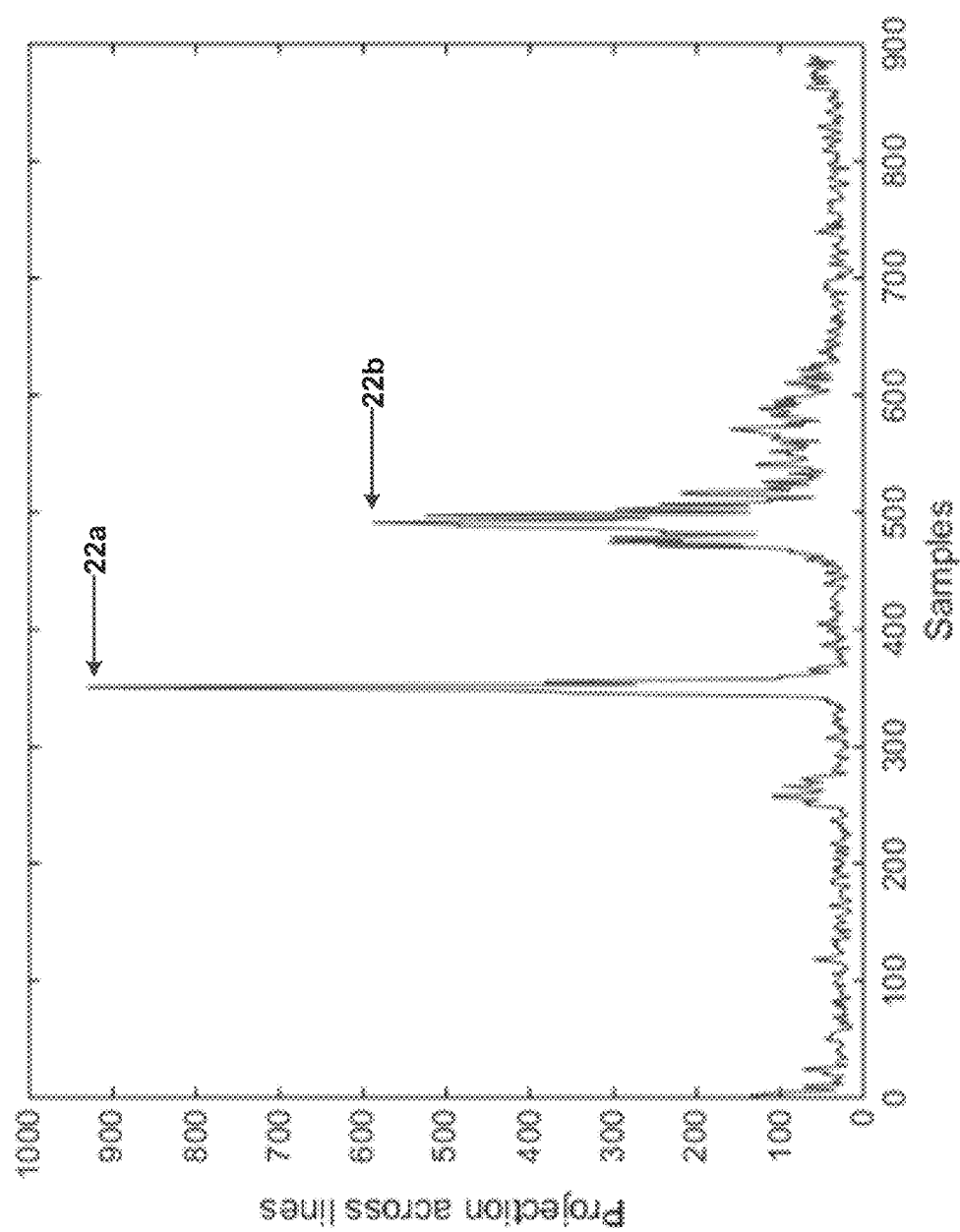
FIG. 3B is a graph illustrating detection of multiple potential struts within a single shadow in accordance with an illustrative embodiment of the disclosure.

FIG. 3B is a graph illustrating detection of multiple potential struts within a single shadow. FIG. 3B is a plot of the projection across the interior shadow scan lines. There are two local maxima 22a and 22b. These maxima correspond to two potential strut locations within the shadow.

Additional filters can be applied to the local maxima to remove false positives. In various embodiments, a local maximum is selected only if it has a signal greater than $1/10^{th}$ (i.e., 10%) of the global peak (largest maximum along the projection). The global peak is the peak with the greatest amplitude. The 10% threshold reduces the chance of selecting spurious local maxima due to noise. The threshold can be set between 5% (i.e., 1/20th) and 10% of the global peak, such as 5%, 6%, 7%, 8%, 9%, or 10%, with 10% being preferred. In various embodiments, if multiple peaks are detected in close proximity to each other, only the largest peak is selected for further analysis.

At Step 190, the selected local maxima are analyzed to determine which maximum has the highest probability of being the true strut based on the information available from the immediate neighborhood of the strut. A relative score is assigned to each strut based on one or more of the following criteria:

1. Proximity to lumen: The selected local maxima are scored based on proximity to the lumen boundary. The local maximum closest to the lumen around the strut shadow receives the highest score, and the local maximum farthest from the lumen around the strut shadow receives the lowest score.
2. Peak strength: The selected local maxima are scored based on peak strength. The local maximum with the highest peak receives the highest score, and the local maximum with the lowest peak receives the lowest score.
3. Degree of malapposition: The selected local maxima are scored based on their apposition, which refers to the state of being in juxtaposition to the lumen. Local maxima that are apposed within a predefined acceptable distance from the lumen or vessel wall receive a higher malapposition score. Struts that are too far away from the lumen or vessel wall (determined by a user specified threshold using one or more interface screens or based on accepted treatment thresholds) are penalized and receive a lower malapposition score as potential false positives. In one embodiment, a strut can either have a malapposition score of 0 or 1 depending on whether it is malapposed or not, respectively.

These scoring criteria are exemplary, and additional scoring criteria based on other strut and shadow features may be used.

Each local maxima gets a combined score which is the linear sum of the abovementioned criteria. At Step 200, the local maximum with the highest score is selected as the valid strut. At Step 210, the remaining local maxima are saved as alternative or backup struts pending further analysis. In the event of a tie, the local maximum closest to the lumen and/or the brightest local maximum are used as tiebreakers. Table 1 provides an exemplary ranking of local maxima for a stent shadow.

TABLE 1

Local maxima ranking for a stent shadow.

|  | Local Maximum 1 | Local Maximum 2 | Local Maximum 3 |
| --- | --- | --- | --- |
| Proximity to Lumen | 3 | 2 | 1 |
| Peak Strength | 2 | 1 | 3 |
| Malapposition | 1 | 0 | 0 |
| Total | 6 | 3 | 4 |

As shown in Table 1, local maximum 1 has the highest total score and therefore would be selected as the candidate valid strut. Local maxima 2 and 3 would be designated as backup struts.

At Step 220, all local maxima (valid strut and any backup struts) undergo multi-frame validation. In this step, adjacent frames are compared to verify that a valid strut in one frame aligns with valid struts selected for adjacent frames. If a valid strut does not align with other cross-frame struts, then the valid strut may be replaced by a backup strut if the backup strut better fits the cross-frame model. One embodiment of the multi-frame validation step can use stent strut geometry and location information. Other embodiments with a bigger set of strut and shadow features can also be used for this step.

Once detected, the valid or chosen struts can be displayed on a user interface, which conveys vital visual aid to the clinician about the precise location of stent struts and whether adjustments may be necessary to optimize and/or speed-up stent placement and reduce the risk of side effects. The user interface can include cross-sectional images, L-Mode images, scan line images, three dimensional renderings, or any other suitable display format for visualizing detected struts.

The detection algorithm accurately identified the location of struts, with a sensitivity of that ranges from greater than about 80% in one embodiment. The detection algorithm accurately identified the location of struts, with a sensitivity of that ranges from greater than about 00% in one embodiment. Sensitivity is the proportion of struts correctly located over the total number of struts (struts correctly located plus struts missed). The positive predictive value is the proportion of struts correctly detected over all positive calls (struts correctly detected plus false positive struts).

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. Some or all of the processing of data collected using an OCT probe and other imaging devices is implemented as a set of computer program instructions that is converted into a computer executable form, stored as such in a computer readable medium, and executed by a processor, for example, under the control of an operating system. Thus, user interface instructions or automated imaging processing of intravascular data received from a cath lag system, for example, are transformed into processor understandable instructions suitable for generating OCT data, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as detected stents, candidate stent struts, FFR data, IVUS data, shadows, pixels, intensity patterns, scores, projections, side branch data, and guidewire data and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

What is claimed is:

1. A method of stent strut detection comprising:
   accessing a plurality of frames of intravascular imaging data, the plurality of frames comprising optical coherency tomography (OCT) scan lines;
   identifying a plurality of shadow regions in the plurality of frames;
   identifying scan lines comprising the plurality of shadow regions,
   analyzing the identified scan lines to determine a set of scan lines comprising scan lines corresponding to interior of a shadow region, wherein the set of scan lines are candidate strut containing scan lines; and
   analyzing the candidate strut containing scan lines to identify location of a stent strut.

2. The method of claim 1, wherein identifying a shadow region comprises eliminating shadow regions corresponding to non-stent features.

3. The method of claim 2, wherein the non-stent features are selected from the group consisting of: a guidewire, a side branch, and combinations thereof.

4. The method of claim 1, comprising eliminating candidate strut shadow scan lines that contain lumen pixels.

5. The method of claim 1, wherein analyzing the candidate strut containing scan lines comprises determining a projection across each of the candidate strut containing scan lines by summing a signal response across the candidate strut containing scan lines.

6. The method of claim 5 comprising identifying up to three local maxima in the projection.

7. The method of claim 6, comprising ranking the local maxima based on peak signal intensity to generate a peak score.

8. The method of claim 7, wherein the ranking is an ordinal ranking, with local maxima having higher peak signal intensity receiving a higher peak score.

9. The method of claim 8 comprising ranking the local maxima based on proximity to a blood vessel wall to generate a proximity score.

10. The method of claim 9, wherein the ranking is an ordinal ranking, with local maxima closer to the blood vessel wall receiving a higher proximity score.

11. The method of claim 10 comprising assigning a malapposition score to each local maxima.

12. The method of claim 11, wherein the malapposition score is binary, with malapposed local maxima receiving a score of zero.

13. The method of claim 12, comprising summing the peak score, the proximity score, and the malapposition score, wherein the local maximum with highest total score is designated as the location of the stent strut.

14. A method of stent strut detection comprising:
    accessing a plurality of frames of intravascular imaging data, the plurality of frames comprising optical coherency tomography (OCT) scan lines;
    identifying a plurality of shadow regions in the plurality of frames;
    eliminating shadow regions corresponding to non-stent features;
    identifying scan lines that correspond to the plurality of shadow regions, wherein the identified scan lines are candidate strut containing scan lines;
    analyzing the candidate strut containing scan lines to identify location of a stent strut; and performing a cross-frame analysis to validate candidate stent struts across multiple frames using one or more geometric features.

15. The method of claim 1, comprising performing a cross-frame analysis to validate candidate stent struts across multiple OCT imaging frames.

16. The method of claim 15, comprising displaying on a graphical user interface the validated stent struts.

17. A computer readable medium comprising non-transitory instructions that when executed cause a processor of an OCT imaging system to perform the steps of claim 1.

18. A method of intravascular stent strut detection comprising:
    storing a plurality of frames of intravascular imaging data in an electronic memory device;
    detecting one or more shadow regions in a first group of frames of the plurality of frames, wherein one or more of the one or more shadow regions corresponds to one or more scan lines;
    determining on a per shadow region basis if a detected shadow region is a guidewire induced region or a side branch induced region;
    generating a set of candidate stent strut shadow regions by excluding detected shadows corresponding to guidewire induced regions or side branch induced regions, wherein each candidate stent strut shadow region comprises a shadow boundary;
    identify scan lines of a candidate stent strut shadow region located within the shadow boundary; and
    performing a cross-frame analysis to validate candidate stent struts across multiple frames using one or more geometric features.

19. The method of claim 18 further comprising validating candidate stent struts identified on scan lines and located within the shadow boundary.

20. The method of claim 19 further comprising displaying the validated candidate stent struts on a user interface display.

* * * * *